US005958946A

United States Patent [19]
Styczynski et al.

[11] Patent Number: 5,958,946
[45] Date of Patent: Sep. 28, 1999

[54] MODULATION OF HAIR GROWTH

[76] Inventors: Peter Styczynski, P.O. Box 387, Mt. Airy, Md. 21771; Gurpreet S. Ahluwalia, 8632 Stableview Court, Gaithersburg, Md. 20882

[21] Appl. No.: 09/009,213

[22] Filed: Jan. 20, 1998

[51] Int. Cl.$^6$ ..................................................... A61K 31/47
[52] U.S. Cl. ........................ 514/311; 514/270; 514/453; 514/456; 514/718; 514/731
[58] Field of Search ..................................... 514/311, 453, 514/456, 718, 270, 731

[56] References Cited

U.S. PATENT DOCUMENTS

| | | |
|---|---|---|
| 3,426,137 | 2/1969 | Philpitt et al. . |
| 4,039,669 | 8/1977 | Beylar et al. . |
| 4,139,638 | 2/1979 | Neri et al. . |
| 4,161,540 | 7/1979 | Neri et al. . |
| 4,191,775 | 3/1980 | Glen . |
| 4,269,831 | 5/1981 | Ferrari et al. . |
| 4,370,315 | 1/1983 | Greff et al. . |
| 4,439,432 | 3/1984 | Peat . |
| 4,508,714 | 4/1985 | Cecic et al. . |
| 4,517,175 | 5/1985 | Iwabuchi et al. . |
| 4,720,489 | 1/1988 | Shander . |
| 4,885,289 | 12/1989 | Breuer et al. . |
| 4,935,231 | 6/1990 | Pigiet . |
| 5,095,007 | 3/1992 | Ahluwalia . |
| 5,096,911 | 3/1992 | Ahluwalia et al. . |
| 5,132,293 | 7/1992 | Shander et al. . |
| 5,143,925 | 9/1992 | Shander et al. . |
| 5,189,212 | 2/1993 | Ruenitz . |
| 5,271,942 | 12/1993 | Haverhagen . |
| 5,300,284 | 4/1994 | Wiechers et al. . |
| 5,364,885 | 11/1994 | Ahluwalia et al. . |
| 5,411,991 | 5/1995 | Shander et al. . |
| 5,455,234 | 10/1995 | Ahluwalia et al. . |
| 5,474,763 | 12/1995 | Shander et al. . |
| 5,554,608 | 10/1996 | Ahluwalia et al. . |
| 5,648,394 | 7/1997 | Boxall et al. . |

FOREIGN PATENT DOCUMENTS

| | | |
|---|---|---|
| 0 413 528 A1 | 2/1991 | European Pat. Off. . |
| 0 532 219 A2 | 3/1993 | European Pat. Off. . |
| 1 458 349 | 12/1976 | United Kingdom . |
| WO 96/10387 | 4/1996 | WIPO . |

OTHER PUBLICATIONS

Pegg et al., "Fundam. Appl. Toxicol.", vol. 32(1):45–32, (1996) (Abstract only).
Andrew G. Messenger, "The Control of Hair Growth: An Overview", The Society for Investigative Dermatology, Inc., 1993.
Green et al., "Cloning and Expression of a Rat Liver Phenobarbital–Inducible UDP–Glucuronosyltransferase (2B12) with Specificity for Monoterpenoid Alcohols", Arch. of Biochem. & Biophysics, vol. 322, Oct. 1, 1995.
Wong et al., "Differential Induction of UDP–Glucuronosyltransferase Activity and Gene Expression in Rat Liver", Pharmaceutical Research, vol. 12, No. 7, 1995.
Sun et al., "Flavonoids increased the activity of Testosterone Glucuronosyltransferase (GT) in prostate cancer cells", Proceedings of the American Association for Cancer Research, vol. 36, Mar. 1995 (Abstract).
Kashfi et al., "Regulation of Uridine Diphosphate Glucuronosyltransferase Expression by Phenolic Antioxidants", Cancer Research, 54, pp. 5856–5859, Nov. 15, 1994.
Pritchard et al., "A Recombinant Phenobarbital–Inducible Rat Liver UDP–Glucoronsyltransferase (UDP–Glucuro–nosyltransferase 2B1) Stably Expressed in V79 Cells Catalyzes . . . " Molecular Pharmacology, 45:42–50, 1993.
Chen et al., "Characterization of a Cloned Human Dihydrotestosterone/Androstanediol UDP–Glucuronosyltransferase and Its Comparison to Other Steroid Isoforms", Biochemistry, vol. 32, No. 40, 10648–57, 1993.
Michael R. Franklin, "Drug Metabolizing Enzyme Induction by Simple Diaryl Pydridines; 2–Substituted Isomers Selectively Increase Only Conjugation Enzyme Activities . . . ", Toxicology and Applied Pharmacology, 111, 1991.
J. Baron, "In situ sites for xenobiotic activation and detoxication: Implications for the differential susceptibility of cells to the toxic . . . ", Progress in Histo–and Cytochemistry, vol. 23, 1991.
Tephyl et al., "UDP–glucuronosyltransferases: a family of detoxifying enzymes", TIPS Reviews, Jul. 1990.
Ritter et al., "Induction of Hepatic Oxidative and Conjugative Drug Metabolism in the Hamster by N–Substituted Imidazoles", Toxicology Letters, 36, pp. 51–59, 1987.
Schweikert et al., Regulation of Human Hair Growth by Steroid Hormones, JCE&M, vol. 38, No. 5, 1974.
Adachi et al., "Human Hair Follicles: Metabolism and Control Mechanisms", Journal of the Society of Cosmetic Chemists, 21, 901–924, Dec. 9, 1970.
Marty E. Sawaya, "Steroid Chemistry and Hormone Controls during the Hair Follicle Cycle", Annals New York Academy of Sciences, pp. 376–384 (Undated).
CA 123:4198, Kudlacek et, 1995.
CA 125:293042, Ahlowaha et al, 1996.

*Primary Examiner*—Rebecca Cook
*Attorney, Agent, or Firm*—Fish & Richardson P.C.

[57] ABSTRACT

Mammalian hair growth may be modulated by applying to the skin a compound that induces or activates the conjugation of an androgen.

39 Claims, No Drawings

MODULATION OF HAIR GROWTH

BACKGROUND OF THE INVENTION

The invention relates to modulating hair growth in mammals.

A main function of mammalian hair is to provide environmental protection. However, that function has largely been lost in humans, in whom hair is kept or removed from various parts of the body essentially for cosmetic reasons. For example, it is generally preferred to have hair on the scalp but not on the face.

Various procedures have been employed to remove unwanted hair, including shaving, electrolysis, depilatory creams or lotions, waxing, plucking, and therapeutic antiandrogens. These conventional procedures generally have drawbacks associated with them. Shaving, for instance, can cause nicks and cuts, and can leave a perception of an increase in the rate of hair regrowth. Shaving also can leave an undesirable stubble. Electrolysis, on the other hand, can keep a treated area free of hair for prolonged periods of time, but can be expensive, painful, and sometimes leaves scarring. Depilatory creams, though very effective, typically are not recommended for frequent use due to their high irritancy potential. Waxing and plucking can cause pain, discomfort, and poor removal of short hair. Finally, antiandrogens—which have been used to treat female hirsutism—can have unwanted side effects.

It has previously been disclosed that the rate and character of hair growth can be altered by applying to the skin inhibitors of certain enzymes. These inhibitors include inhibitors of 5-alpha reductase, ornithine decarboxylase, S-adenosylmethionine decarboxylase, gamma-glutamyl transpeptidase, and transglutaminase. See, for example, Breuer et al., U.S. Pat. No. 4,885,289; Shander, U.S. Pat. No. 4,720,489; Ahluwalia, U.S. Pat. No. 5,095,007; Ahluwalia et al., U.S. Pat. No. 5,096,911; Shander et al., U.S. Pat. No. 5,132,293; and Shander et al., U.S. Pat. No. 5,143,925.

The growth of hair results from many complex and interactive processes. In one process sex steroid androgens, particularly testosterone, act on, for example, beard hair follicles on the face to stimulate hair growth. But these same androgens can inhibit hair growth on the scalp, particularly in those that have a genetic predisposition for male-pattern baldness or androgenetic alopecia.

Cytochrome P450s, epoxide hydrolases, glutathione-S-transferases, uridine diphosphate-glucuronosyltransferases (UGTs), and sulfotransferases (STs) are families of enzymes that are involved in the metabolism of xenobiotics and other substances that are endogeneous to the human body. Generally, the enzymes catalyze the conversion of a substrate (e.g., a particular steroid) to a form that is more readily eliminated from the body. For example, glutathione-S-tranferases catalyze the conjugation of the substrate with glutathione; UGTs catalyze the conjugation of substrate with glucuronic acid; and STs catalyze the conjugation of the substrate with a sulfonate moiety. It is believed that these substrate conjugates are more water soluble than the substrate itself, and thus more readily eliminated from the body. Some of these enzymes can be induced by compounds, such as 3-methylcholanthrene and phenobarbital.

Steroids are substrates for several isoforms of UGT, with overlapping specificities. For example, rat liver UGTr-3 catalyzes the glucuronidation of dihydrotestosterone, testosterone and β-estradiol, whereas in addition to these steroids UGTr-2 also catalyzes 4-hydroxybiphenyl, chloramphenicol and 4-methylumbelliferone glucuronoconjugation (Chen et al., Biochem. 32: 10648–10657).

SUMMARY OF THE INVENTION

In one aspect, the invention features modulating hair growth by topical application of a compound that induces or activates the conjugation of an androgen (e.g., testosterone) that is involved in hair growth. By "induces" or "activates", we mean that the compound increases the conjugating enzyme levels in the hair follicle cells and/or increases the catalytic activity of the conjugating enzyme for conjugation. The compound may, for example, induce or activate a UGT or an ST for which the androgen serves as the substrate.

The modulation in hair growth depends on whether the hair growth selected for treatment is androgen-stimulated hair growth (e.g., beard hair and torso hair generally in humans) or hair growth that is not androgen-stimulated (e.g., scalp hair in humans). Topical application of the compound in a dermatologically acceptable vehicle to an area of skin having androgen-stimulated hair growth generally causes a reduction in hair growth. Topical application of the compound in a dermatologically acceptable vehicle to an area of skin having hair growth (i.e., from the scalp) that is reduced in the presence of androgens, (e.g., because of androgenic alopecia) generally causes an increase in hair growth.

In another aspect, the invention features modulating hair growth by topical application of a compound that induces or activates a UGT.

In another aspect, the invention features modulating hair growth by topical application of a compound that induces or activates an ST.

In another aspect, the invention features modulating hair growth by topical application of a compound that induces or activates the conversion of an androgen involved in hair growth to a less active (e.g., more water soluble) metabolite.

Other features and advantages of the invention will be apparent from the Description of Preferred Embodiments thereof, and from the claims.

DESCRIPTION OF PREFERRED EMBODIMENTS

Compounds that activate or induce UGTs are known. Such compounds include ethoxyquin, 5,7-dihydroxy-4'-methoxyflavone, butylhydroxyanisole, phenobarbital, naringenin, butylhydroxytoluene, flavone, tioconazole, trans-1,2-bis(2-pyridyl)ethylene, 7,4'-isoflavandiol, (equol), galangin, 7-hydroxy-4'-methoxyisoflavone (formononetin), 5,4'-dihydroxy-7-methoxyisoflavone (prunetin), and daidzein. These compounds induce UGTs relevant to testosterone gluconionidation.

Examples of androgens that may be conjugated include testosterone, dihydrotestosterone, androstenedione, androstenediols, and dehydroepiandrosterone.

It is believed that the compounds act according to the pathway shown below (in which testosterone is used as an example):

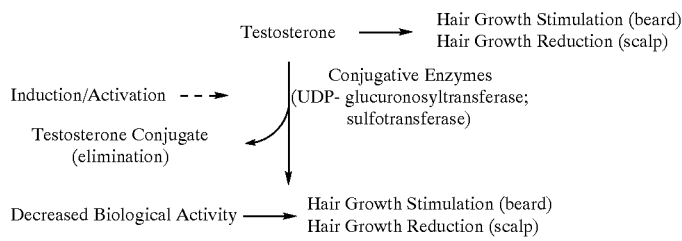

The compound may induce or activate, for example, UGTs that catalyze the conjugation of testosterone with glucuronic acid (donated from uridine diphosphoglucuronic acid) or STs that catalyze the conjugation of testosterone with a sulfonate group (donated from 3'-phosphoadenosine 5'-phosphosulfate).

The compound preferably is incorporated in a topical composition that includes a non-toxic dermatologically acceptable vehicle or carrier which is adapted to be spread upon the skin. Examples of suitable vehicles are acetone, alcohols, or a cream, lotion, or gel which can effectively deliver the active compound. A vehicle is disclosed in U.S. Pat. No. 5,648,394. In addition, a penetration enhancer may be added to the vehicle to further enhance the effectiveness of the formulation.

The concentration of the compound in the composition may be varied over a wide range up to a saturated solution, preferably from 0.1% to 30% by weight or even more; the reduction or increase in hair growth rises as the amount of inhibitor applied increases per unit area of skin. The maximum amount effectively applied is limited only by the rate at which the compound penetrates the skin. The effective amounts may range, for example, from 10 to 3000 micrograms or more per square centimeter of skin.

A composition may include more than one of the compounds.

The composition should be topically applied to a selected area of the body from which it is desired to reduce hair growth (if the hair growth is androgen-stimulated hair growth) or increase hair growth (if the hair loss is androgen dependent). For example, in humans the composition can be applied to the face, particularly to the beard area of the face, i.e., the cheek, neck, upper lip, and chin to obtain a reduction in hair growth. The composition can also be applied to the legs, arms, torso or armpits to obtain a reduction in hair growth. The composition can be applied to the scalp to obtain an increase in hair growth. The composition is particularly suitable for reducing the growth of unwanted hair in women suffering from hirsutism or other similar conditions.

In humans, the composition, for example, may be applied once or twice a day, or even more frequently, for two weeks to six months (e.g., three months) to achieve a perceived effect. Reduction in hair growth is demonstrated when the frequency of hair removal is reduced or the subject perceives less hair on the treated site, or quantitatively, when the weight of hair removed by shaving (i.e., hair mass) is reduced. Increase in hair growth is demonstrated when the opposite effect is observed.

Male intact Golden Syrian hamsters are considered acceptable models for human beard hair growth and other androgen-stimulated hair growth in that they display oval shaped flank organs, one on each side, each about 8 mm. in major diameter, which grow thick black and coarse hair similar to human beard hair. These organs produce hair in response to androgens in the hamster. To evaluate the effectiveness of a composition in reducing androgen-stimulated hair growth, the flank organs of each of a group of hamsters are shaved. To one organ of each animal 10 µl. of composition vehicle alone once a day is applied, while to the other organ of each animal an equal amount of the composition (including the relevant compound or compounds). After thirteen applications (one application per day for five days a week), the flank organs are shaved and the amount of recovered hair (hair mass) from each is weighed. Percent-reduction of hair growth is calculated by subtracting the hair mass (mg) value of the test compound treated side from the hair mass value of the vehicle treated side; the delta value obtained is then divided by the hair mass value of the vehicle treated side, and the resultant number is multiplied by 100.

The above-described assay will be referred to herein as the "Golden Syrian hamster" assay. Preferred compositions provide a reduction in hair growth of at least about 30%, more preferably at least about 50%, and most preferably at least about 60% when tested in the Golden Syrian hamster assay.

A number of compositions containing compounds that induce or activate UGTs for which testosterone is a substrate were tested in the Golden Syrian hamster assay; the results are provided in Table I:

TABLE I

| Compound | Vehicle | Left(mg) | Right(mg) | % Inhibition |
| --- | --- | --- | --- | --- |
| ethoxyquin | A | 0.55 ± .16 | 2.41 ± .11 | 75 ± 7 |
| 5,7-dihydroxy-4'-methoxyflavone | B | 1.00 ± .22 | 2.61 ± .27 | 62 ± 9 |
| butylhydroxyanisole | A | 0.92 ± .24 | 2.27 ± .11 | 61 ± 9 |
| phenobarbital | A | 0.89 ± .16 | 1.88 ± .24 | 51 ± 11 |
| naringenin | A | 1.42 ± .18 | 2.46 ± .20 | 40 ± 8 |
| butylhydroxytoluene | C | 1.74 ± .38 | 2.05 ± .36 | 22 ± 18 |
| flavanone | C | 1.91 ± .22 | 2.39 ± .22 | 17 ± 10 |

All compounds were administered as a 10% does. Vehicle A = ethanol 80%, $H_2O$ 17.5%, propylene glycol dipelargonate 2%, propylene glycol 0.5%; B = ethanol 70%, dimethylsulfoxamine 30%; C = propylene glycol 50%, ethanol 25%, dimethylsulfoxide 25%.

An assay was performed to evaluate whether some of the compounds tested in the Golden Syrian Hamster assay caused an induction of testosterone glucuronide formation.

Flank organ homogenates were prepared by adding 4 flank organs into 2 mL of a buffer containing 25 mM Tris/50 mM sucrose, pH 7.4 and homogenized with a Polytron (Brinkman Instruments) while keeping the mixture on ice. The glucuronidation of testosterone was measured by incubating the 20 µl of the flank organ protein (1 mg/ml) with [$^{14}$C]-testosterone testosterone 125 µM and UDP-glucuronic acid (5 mM) in the presence of buffer containing 0.5M Tris, pH 7.5 and 0.1M $MgCl_2$. The total reaction mixture volume was 100 µl. Assay mixtures were incubated at 37° C. for 60 minutes, and reactions were stopped with the addition of 3.5 ml methylene chloride. An aqueous carrier (250 µl water) was added to each reaction mixture which was then shaken and centrifuged. The unmetabolized [$^{14}$C]-testosterone remained in the organic phase whereas the testosterone glucuronide partitioned into the aqueous phase, and was quantitated by scintillation spectrometry. The results are provided in Table II:

TABLE II

| Compound | % Induction |
| --- | --- |
| ethoxyquin | 214 |
| butylhydroxyanisole | 178 |
| 5,7-dihydroxy-4'-methoxyflavone | 120 |
| phenobarbital | 113 |

It was believed that the diversion of testosterone away from its biologically active species to a glucuronide or sulfonate conjugate would have effects on the flank organs of the Golden Syrian hamster since testosterone is known to regulate the existence of these unique organs. The diameter of flank organs were assessed using a caliper following topical treatment of the hamsters with ethoxyquin or 5,7-dihydroxy-4'-methoxyflavone as described in the hair mass assay section. A decrease in flank organ diameter was demonstrated following topical application of the compounds (Table III). These data are consistent with the hypothesis that suggests that local induction of conjugating enzymes, such as UGTs, can diminish the biological activity of testosterone.

TABLE III

| Treatment | Treated FO (mm) | Vehicle FO (mm) | Decrease (mm) | % Decrease |
| --- | --- | --- | --- | --- |
| ethoxyquin | 7.18 ± .26 | 8.83 ± .28 | 1.65 ± .37 | 19 ± 4 |
| 5,7-dihydroxy-4'-methoxyflavone | 8.04 ± .29 | 9.08 ± .43 | 1.04 ± .46 | 12 ± 5 |

Other embodiments are within the claims.

We claim:

1. A method of inducing or activating uridine diphosphate-glucouronosyltransferase to catalyze conjugation of an androgen involved in hair growth with glucuronic acid or inducing or activating a sulfotransferase to catalyze conjugation of an androgen involved in hair growth with a sulfonate to reduce mammalian androgen-stimulated hair growth, which comprises selecting an area of skin from which hair grows in response to androgen-stimulation and from which reduced hair growth is desired; and applying to said area of skin a dermatologically acceptable composition comprising an effective amount of a compound that induces or activates said uridine diphosphate-glucouronosyltransferase to catalyze conjugation of said androgen with glucuronic acid or induces or activates said sulfotransferase to catalyze conjugation of said androgen with a sulfonate so that hair growth is reduced from said area of skin.

2. A method of inducing or activating uridine diphosphate-glucouronosyltransferase to catalyze conjugation of an androgen involved in hair growth with glucuronic acid or inducing or activating a sulfotransferase to catalyze conjugation of an androgen involved in hair growth with a sulfonate to increase growth of mammalian hair that does not grow in response to androgen-stimulation, which comprises selecting an area of skin from which hair that does not grow in response to androgen-stimulation and from which increased hair growth is desired; and applying to said area of skin a dermatologically acceptable composition comprising an effective amount of a compound that induces or activates said uridine diphosphate-glucouronosyltrasferase to catalyze conjugation of said androgen with glucuronic acid or induces or activates said sulfotransferase to catalyze conjugation of said androgen with a sulfonate so that hair growth is increased from said area of skin, wherein said compound is not flavone or a flavone derivative.

3. The method of claim 1 or 2, wherein said compound comprises ethoxyquin.

4. The method of claim 1, or wherein said compound comprises 5,7-dihydroxy-4'-methoxyflavone.

5. The method of claim 1 or 2, wherein said compound comprises butylhydroxyanisole.

6. The method of claim 1 or 2, wherein said compound comprises phenobarbital.

7. The method of claim 1, wherein said compound comprises naringenin.

8. The method of claim 1 or 2, wherein said compound comprises butylhydroxytoluene.

9. The method of claim 1, wherein said compound comprises flavone.

10. The method of claim 1 or 2, wherein said compound comprises tioconazole.

11. The method of claim 1, wherein said compound comprises trans-1,2-bis(2-pyridyl)ethylene.

12. The method of claim 1, wherein said compound comprises 7,4'-isoflavandiol.

13. The method of claim 1, wherein said compound comprises galangin.

14. The method of claim 1, wherein said compound comprises 7-hydroxy-4'-methoxyisoflavone.

15. The method of claim 1, wherein said compound comprises 5,4'-dihydroxy-7-methoxyisoflavone.

16. The method of claim 1, wherein said compound comprises daidzein.

17. The method of claim 1, wherein said compound induces or activates the diphosphate-glucouronosyltransferase to catalyze conjugation of said androgen with glucuronic acid.

18. The method of claim 2, wherein said compound induces or activates the sulfotransferase to catalyze conjugation of said androgen with a sulfonate.

19. The method of claim 1 or 2, wherein said androgen comprises testosterone.

20. The method of claim 1 or 2, wherein the concentration of said compound in said composition is between 0.1% and 30%.

21. The method of claim 1 or 2, wherein the composition provides a reduction in hair growth of at least 15% when tested in the Golden Syrian hamster assay.

22. The method of claim 1 or 2, wherein the composition provides a reduction in hair growth of at least 40% when tested in the Golden Syrian hamster assay.

23. The method of claim 1 or 2, wherein said mammal is a human.

24. The method of claim 1, wherein the area of skin is on the face of the human.

25. The method of claim 24, wherein said human is a woman suffering from hirsutism.

26. The method of claim 2, wherein the area of skin is on the scalp of a human.

27. A method of conjugating an androgen that stimulates androgen-stimulated hair growth to produce a conjugate of said androgen that is more readily eliminated from the body than said androgen to reduce mammalian androgen-stimulated hair growth, which comprises selecting an area of skin from which hair grows in response to androgen-stimulation and from which reduced hair growth is desired; and applying to said area of skin a dermatoligically acceptable composition comprising an effective amount of a compound that induces or activates the conjugation of said androgen to produce said conjugate so that hair growth is reduced from said area of skin.

28. The method of claim 27, wherein the area of skin is on the face of a human.

29. A method of conjugating an androgen that retards growth of hair that does not grow in response to androgen-stimulation to increase growth of mammalian hair that does not grow in response to androgen-stimulation, which comprises selecting an area of skin from which hair does not grow in response to androgen-stimulation and from which increased hair growth is desired; and applying to said area of skin a dermatologically acceptable composition comprising an effective amount of a compound that induces or activates the conjugation of said androgen to produce said conjugate so that hair growth is increased from said area of skin, wherein said compound is not flavone or a flavone derivative.

30. The method of claim 29, wherein the area of skin includes the scalp of a human.

31. The method of claim 27 or 29, wherein the compound is an inducer or activator of an androgen conjugation enzyme.

32. The method of claim 31, wherein the androgen comprises a testosterone.

33. The method of claim 31, wherein the androgen comprises dihydrotestosterone.

34. The method of claim 31, wherein the androgen comprises an androgen selected from the group consisting of androstenedione, androstenediols, and dehydroepiandrosterone.

35. A method of inducing or activating conversion of testosterone to a less active metabolite to reduce mammalian androgen-stimulated hair growth, which comprises selecting an area of skin from which hair grows in response to androgen-stimulation and from which reduced hair growth is desired; and applying to said area of skin a dermatologically acceptable composition comprising an effective amount of a compound that induces or activates the conversion of testosterone to said less active metabolite so that the hair growth is reduced form the area of skin.

36. The method of claim 35, wherein the area of skin is on the face of a human.

37. The method of claim 35, wherein the less active metabolite comprises a compound that is more water soluble than testosterone.

38. A method of inducing or activating conversion of testosterone to a less active metabolite to increase hair growth form the scalp of a human, which comprises selecting an area of the scalp of a human and from which increase hair growth is desired; and applying to the area of the scalp a dermatologically acceptable composition comprising an effective amount a compound that induces or activates the conversion of testosterone to said less active metabolite so that hair growth increases from the area of the scalp, wherein said compound is not flavone or a flavone derivative.

39. The method of claim 38, wherein the less active metabolite comprises a compound that is more water soluble than testosterone.

* * * * *

(12) EX PARTE REEXAMINATION CERTIFICATE (5588th)
United States Patent
Styczynski et al.

(10) Number: US 5,958,946 C1
(45) Certificate Issued: Oct. 31, 2006

(54) MODULATION OF HAIR GROWTH

(75) Inventors: Peter Styczynski, Mt. Airy, MD (US); Gurpreet S. Ahluwalin, Gaithersburg, MD (US)

(73) Assignee: The Gillette Company, Boston, MA (US)

Reexamination Request:
No. 90/006,885, Dec. 5, 2003

Reexamination Certificate for:
Patent No.: 5,958,946
Issued: Sep. 28, 1999
Appl. No.: 09/009,213
Filed: Jan. 20, 1998

(51) Int. Cl.
*A61K 31/47* (2006.01)

(52) U.S. Cl. .................. 514/311; 514/270; 514/453; 514/456; 514/719; 514/731

(58) Field of Classification Search .................. 514/311, 514/270, 453, 456, 719, 731
See application file for complete search history.

(56) References Cited

U.S. PATENT DOCUMENTS

| | | | |
|---|---|---|---|
| 4,877,789 A | 10/1989 | Shroot et al. | |
| 5,438,058 A | 8/1995 | Dufetel | |
| 5,466,694 A | 11/1995 | Terranova et al. | |
| 5,468,474 A | 11/1995 | Honda et al. | |
| 5,468,897 A | 11/1995 | Shroot et al. | |
| 5,470,861 A | 11/1995 | Harmon | |
| 5,583,126 A | 12/1996 | Daynes et al. | |
| 5,639,785 A | 6/1997 | Kung | |
| 5,665,335 A | 9/1997 | Bombardelli et al. | |
| 5,928,654 A | 7/1999 | Duranton | |
| 6,239,170 B1 | 5/2001 | Ahluwalia et al. | |

FOREIGN PATENT DOCUMENTS

| | | |
|---|---|---|
| EP | 0 648 488 | 4/1995 |
| EP | 0 747 048 A2 | 12/1996 |
| EP | 0 800 815 A2 | 10/1997 |
| JP | 59-155314 | 4/1984 |
| JP | 1-96126 | 4/1989 |
| JP | 2-17115 | 1/1990 |
| WO | WO 94/27563 | 12/1994 |
| WO | WO 94/27586 | 12/1994 |
| WO | WO 96/10387 | 4/1996 |
| WO | WO 96/26712 | 9/1996 |
| WO | WO 96/39832 | 12/1996 |
| WO | 0 800 815 | 10/1997 |
| WO | WO 98/08503 | 3/1998 |
| WO | WO 99/22728 | 5/1999 |

OTHER PUBLICATIONS

Laighton et al., "Inhibition of Mammalian 5–Lipoxygenase and Cyclo–Oxygenase by Flavonoids and Phenolic Dietary Additives", Biochemical Pharmacology, vol. 42, No. 9, pp. 1673–1681, 1991.

J. Baron, "In situ sites for xenobiotic activation and detoxication: Implications for the differential susceptibility of cells to the toxic", Progress in Histo–and Cytochemistry, vol. 23, 1991.

Tephly et al., "UDP–Glucuronosyltransferases: A family of detoxifying enzymes", TIPS Reviews, Jul. 1990.

Walle et al., "Quercetin, a Potent and Specific Inhibitor of the Human P–Form Phenolsulfotransferase", Biochemical Pharmacology, vol. 50, No. 5, pp. 731–734, 1995.

Evans et al., "Inhibition of 5α–Reductase in Genital Skin Fibroblasts and Prostate Tissue by Dietary Lignans and Isoflavonoids", Journal of Endocrinology, 147, pp. 295–302, 1995.

Kalinina et al., "On the Role of UDP–Glucuronosyl Transferases and Sulfotransferases in the Inhibitory Effect of Butylated Hydroxytoluene on the Mutagenicity of Carcinogenic Nitroso Compounds and Cyclophosphamide", All–Union Res Inst. Biotechnol, Moscow, USSR, pp. 220–225, 1989 (Abstract Only).

Golf et al., "Properties and Biochemical Characterization of NADH—5α–Reductase from Rat Liver Microsomes", Biol. Chem. Hoppe–Seyler, vol. 366, pp. 647–653, Jul. 1985.

*Primary Examiner*—Thurman K. Page

(57) ABSTRACT

Mammalian hair growth may be modulated by applying to the skin a compound that induces or activates the conjugation of an androgen.

1

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 2, 18, 26, 29 and 30 is confirmed.

Claims 4, 8, 9 and 12–16 are cancelled.

Claims 1, 10, 21, 22, 27, 35 and 38 are determined to be patentable as amended.

Claims 3, 5–7, 11, 17, 19, 20, 23–25, 28, 31–34, 36, 37 and 39, dependent on an amended claim, are determined to be patentable.

New claims 40–49 are added and determined to be patentable.

1. A method of inducing or activating uridine diphosphate-glucouronosyltransferase to catalyze conjugation of an androgen involved in hair growth with glucuronic acid or inducing or activating a sulfotransferase to catalyze conjugation of an androgen involved in hair growth with a sulfonate to reduce mammalian androgen-stimulated hair growth, which comprises selecting an area of skin from which hair grows in response to androgen-stimulation and from which reduced hair growth is desired; and applying to said area of skin a dermatologically acceptable composition comprising an effective amount of a compound that induces or activates said uridine diphosphate-glucouronosyltransferase to catalyze conjugation of said androgen with glucuronic acid or induces or activates said sulfotransferase to catalyze conjugation of said androgen with a sulfonate so that hair growth is reduced from said area of skin, *wherein said compound is not flavone, a flavone derivative, or tioconazole.*

10. The method of claim [1 or] 2, wherein said compound comprises tioconazole.

21. The method of claim 1 [or 2], wherein the composition provides a reduction in hair growth of at least 15% when tested in the Golden Syrian hamster assay.

22. The method of claim 1 [or 2], wherein the composition provides a reduction in hair growth of at least 40% when tested in the Golden Syrian hamster assay.

27. A method of conjugating an androgen that stimulates androgen-stimulated hair growth to produce a conjugate of said androgen that is more readily eliminated from the body than said androgen to reduce mammalian androgen-stimulated hair growth, which comprises selecting an area of skin from which hair grows in response to androgen-stimulation and from which reduced their hair growth is desired; and applying to said area of skin a dermatoligically acceptable composition comprising an effective amount of a compound that induces or activates the conjugation of said androgen to produce said conjugate so that hair growth is reduced from said area of skin, *wherein said compound is not flavone, a flavone derivative, or tioconazole.*

35. A method of inducing or activating conversion of testosterone to a less active metabolite to reduce mammalian androgen-stimulated hair growth, which comprises selecting an area of skin from which hair grows in response to androgen-stimulation and from which reduced hair growth is desired; and applying to said area of skin a dermatologically acceptable composition comprising an effective amount of a compound that induces or activates the conversion of testosterone to said less active metabolite so that the hair growth is reduced form the area of skin, *wherein said compound is not flavone, a flavone derivative, or tioconazole.*

38. A method of inducing or activating conversion of testosterone to a less active metabolite to increase hair growth [form] *from* the scalp of a human, which comprises selecting an area of the scalp of a human and from which increase hair growth is desired; and applying to the area of the scalp a dermatologically acceptable composition comprising an effective amount a compound that induces or activates the conversion of testosterone to said less active metabolite so that hair growth increases from the area of the scalp, *wherein said compound is not flavone or flavone derivative.*

*40. A method of inducing or activating conversion of testosterone to a less active metabolite to reduce mammalian androgen-stimulated hair growth, which comprises selecting an area of skin from which hair grows in response to androgen-stimulation and from which reduced hair growth is desired; and applying to said area of skin a dermatologically acceptable composition comprising an effective amount of a compound that induces or activates the conversion of testosterone to said less active metabolite so that the hair growth is reduced from the area of skin, wherein said compound is not a lipoxygenase inhibitor or tioconazole.*

*41. The method of claim 40, wherein the composition provides a reduction in hair growth of at least 15% when tested in the Golden Syrian hamster assay.*

*42. The method of claim 40, wherein the composition provides a reduction in hair growth of at least 40% when tested in the Golden Syrian hamster assay.*

*43. The method of claim 40, wherein said mammal is a human.*

*44. The method of claim 40, wherein the area of skin is on the face of the human.*

*45. The method of claim 40, wherein said human is a woman suffering from hirsutism.*

*46. A method of conjugating an androgen that stimulates androgen-stimulated hair growth to produce a conjugate of said androgen that is more readily eliminated from the body than said androgen to reduce mammalian androgen-stimulated hair growth, which comprises*

*selecting an area of skin from which hair grows in response to androgen-stimulation and from which reduced hair growth is desired; and* applying to said area of skin a dermatologically acceptable composition comprising an effective amount of a compound that induces or activates the conjugation of said androgen to produce said conjugate so that hair growth is reduced from said area of skin, wherein said compound is not a lipoxygenase inhibiting or tioconazole.

47. The method of claim 46, wherein the area of skin is on the face of a human.

48. A method of inducing or activating uridine diphosphate-glucouronosyltransferase to catalyze conjugation of an androgen involved in hair growth with glucuronic acid or inducing or activating a sulfotransferase to catalyze conjugation of an androgen involved in hair growth with a sulfonate to reduce mammalian androgen-stimulated hair growth, which comprises selecting an area of skin from which hair grows in response to androgen-stimulation and from which reduced hair growth is desired; and applying to said area of skin a dermatologically acceptable composition comprising an effective amount of a compound that induces or activates said uridine diphosphate-glucouronosyltransferase to catalyze conjugation of said androgen with glucuronic acid or induces or activates said sulfotransferase to catalyze conjugation of said androgen with a sulfonate so that the hair growth is reduced from the area of skin, wherein said compound is not a lipoxygenase inhibitor or tioconazole.

49. The method of claim 48, wherein the area of skin is on the face of a human.

* * * * *